United States Patent [19]

Granados

[11] Patent Number: 5,300,435
[45] Date of Patent: Apr. 5, 1994

[54] TRICHOPLUSIA NI CELL LINE WHICH SUPPORTS REPLICATION OF BACULOVIRUSES

[75] Inventor: Robert R. Granados, Ithaca, N.Y.

[73] Assignee: Boyce Thompson Institute for Plant Research, Inc., Ithaca, N.Y.

[21] Appl. No.: 938,821

[22] Filed: Dec. 1, 1992

Related U.S. Application Data

[60] Division of Ser. No. 839,918, Feb. 21, 1992, which is a continuation-in-part of Ser. No. 760,697, Sep. 16, 1991, abandoned.

[51] Int. Cl.$^5$ .......................... C12N 5/00; C12N 1/36
[52] U.S. Cl. .................................. 435/240.2; 435/245
[58] Field of Search ........... 435/240.2, 240.21, 240.31, 435/245, 235.1

[56] References Cited

U.S. PATENT DOCUMENTS 5,024,947  6/1991  Inlow et al. .................... 435/240.31

OTHER PUBLICATIONS

Rockford et al., In Vitro, vol. 20 No. 11 (Nov. 1984) pp. 823–825.
Granados et al., Virology, 152 (1986) pp. 472–476.
Jakoby et al., *Methods in Enzymology,* vol. LVIII, published 1979, pp. 450–466.
Hink, W. F. et al., Expression of Three Recombinant Proteins Using Baculoviurs Vectors in 23 Insect Cell Lines, biotechnol. Prog, 1991, 7, 9–14.
Wickham, T. J. et al., Screening of Insect Cell Lines for the Recombinant Proteins and Infectious Virus in the Baculovirus Expression System, Biotechnol. Prog. 1992, 8, 391–396.
Gibco Laboratories, Sf-900 Serum-Free Insect Cell Culture Medium with L-glutamine Catalog Number 350-0900, Oct. 1989, 4 pages.

*Primary Examiner*—Douglas W. Robinson
*Assistant Examiner*—Susan M. Dadio
*Attorney, Agent, or Firm*—Barnard, Brown & Michaels

[57] ABSTRACT

An insect cell line has been established and characterized, derived from embryonic tissue (BTI-TN-5B1-4, ATCC CRL 10859) of *Trichoplusia ni* (cabbage looper). The line is susceptible to various baculoviruses, including TnSNPV and AcMNPV, and may be used to replicate such viruses for use as insecticides or otherwise.

4 Claims, No Drawings

TRICHOPLUSIA NI CELL LINE WHICH SUPPORTS REPLICATION OF BACULOVIRUSES

This is a divisional patent application of copending patent application Ser. No. 07/839,918, filed Feb. 21, 1992, which is a continuation-in-part of copending patent application Ser. No. 07/760,697, filed Sep. 16, 1991, now abandoned.

BACKGROUND OF THE INVENTION

1. Field of the Invention

This invention relates to cell lines developed from differentiated tissue of insects, including midgut tissue; particularly, to cell lines which are susceptible to baculoviruses and may be used to replicate such viruses.

2. Abbreviations

Abbreviations or definitions used in the disclosure are as follows: AcMNPV, *Autographa californica* multiply-enveloped nuclear polyhedrosis virus; TnSNPV, *Trichoplusia ni* singly-enveloped nuclear polyhedrosis virus; MOI, multiplicity of infection; LDH, lactate dehydrogenase; MDH, malate dehydrogenase; NPV, nuclear polyhedrosis virus.

3. Description of the Related Art

Insect cell culture has been used broadly in insect virology research since the first insect cell line was established in 1962 (Grace, T.D.C., *Establishment of four strains of cells from insect tissue grown in vitro*, Nature, 195:788-789). The general use of tissue cell lines for the culture or replication of pathogenic microorganisms is well established, and production of viral insecticides in cell culture has many advantages over their cultivation in vivo ((Weiss, S. A. and J. L. Vaughn, *Cell culture methods for large-scale propagation of baculovirus*, in "The Biology of Baculoviruses," vol. II "Practical Application for Insect Control" (Granados and Federici, eds., CRC Press, Boca Raton, Fla.), pp. 63-87 (1986)) and (Granados et al., *Production on viral agents in invertebrate cell cultures*, in "Biotechnology in Invertebrate Pathology and Cell Culture" (Maranorosch, K., ed., Academic Press, San Diego/N.Y.), pp. 167-181, (1987)). However, specific microorganisms cannot be cultured in all cell lines, even in all cell lines from the same order. Vaughn, in *Invertebrate Tissue Culture, Research Applications* (Academic Press, N.Y./London, 1976, pp. 295-303) discusses the development of insect cell lines and notes that, for example, cell lines from *Heliothis zea* are not capable of complete replication of the nuclear polyhedrosis virus obtained from *Heliothis zea* itself. It should be apparent from the above that the ability of a given cell line to replicate a given microorganism cannot be predicted from results in cell lines of different species or in different lines from the same species.

In recent years, baculovirus expression vectors have been widely used as vectors for foreign gene expression in insect cells (Luckow, V. A. and M. D. Summers, *High level expression of nonfused foreign genes with Autographa californica nuclear polyhedrosis virus expression vectors*, Virology, 170:311-39 (1988)). Therefore, insect cell culture has become more important as a potentially attractive system for producing viral insecticides and expressing foreign gene products of interest in the areas of biology, medicine, and agriculture.

In addition, *Bacillus thuringiensis*, a gram-positive soil bacterium, has been found to produce crystalline inclusions during sporulation, which consists of insecticidal proteins exhibiting a highly specific insecticidal activity (Aronson et al., *Bacillus thuringiensis and related insect pathogens*, Microbiol. Rev. 50:1-24 (1986)), and many *B. thuringiensis* strains with different insect hosts have been identified (Burges, H. D., ed., *Microbial Control of Pests and Plant Diseases* 1970-1980. Academic Press, Inc., London (1981)). The cloning of these insecticidal crystal protein genes and their expression in plant-associated microorganisms or transgenic plants has provided potentially powerful alternative strategies for the protection of crops against insect damage (Hofte and Whiteley, *Insecticidal crystal proteins of Bacillus thuringiensis*, Microbiol. Rev. 53:242 (1989)). These crystal proteins act on the midgut cells of the insects, binding to specific midgut cell membrane receptors (Hofmann et al., *Specificity of Bacillus thuringiensis δ-endotoxins is correlated with the presence of high-affinity binding sites in the brush border membrane of target insect midguts*, Proc. Natl. Acad. Sc. 85:7844-7848 (1988)), causing the said midgut cells to swell and burst, and the insect stops eating and dies (Hofte and Whiteley, p. 242 (1989)).

Prior to this invention, no cell line had been established from midgut tissue of any insect species, and this hampered studies of the mode of action of these crystal proteins (Hofte and Whiteley, pp. 242-255 (1989)).

Cell lines have been established from other types of tissue from several species of the order Lepidoptera, which includes some of the most significant agricultural pests. Lynn et al. reported lines from embryos and fat body tissue of *Lymantria dispar*, and from the testes of *Heliothis virescens*, in 1988. Mitsuhashi established a cell line from fat body tissue of *Leucania separata* in 1983. Hink established the first such line from *Trichoplusia ni*, the cabbage looper, in 1970; it was derived from ovarian tissue.

Up to the time of this invention, a midgut cell line of the cabbage looper had not been established. Harrap and Robertson, as early as 1968, indicated that nuclear polyhedrosis viruses (NPVs) may infect a larger percentage of midgut cells in vivo, than fat body cells in vivo (Harrap, K. A. and J. S. Robertson, *A possible infection pathway in the development of a nuclear polyhedrosis virus*, J. gen. Virol. 3:221-225 (1968)), making a midgut cell line, which may be used to reproduce baculoviruses, even more attractive.

Cell lines from *Trichoplusia ni* eggs have been established and infected ((Rochford et al., *Establishment of a cell line from embryos of the Cabbage Looper, Trichoplusia Ni (Hubner)*, In Vitro 20: 823-825 (1984)) and (Granados et al , *Replication of the Trichoplusia ni Granulosis and Nuclear Polyhedrosis Viruses in cell cultures*, Virology 152: 472-476 (1986))), however, up to the time of this invention, a *Trichoplusia ni* embryonic cell line which is highly susceptible to numerous baculoviruses and efficiently supports replication of baculoviruses had not been established. Rochford et al. (1984) developed a *Trichoplusia ni* egg cell line (IPLB-TN-R) that is susceptible to only one of six baculoviruses tested, the *Autographa californica* multiply-enveloped nuclear polyhedrosis virus (AcMNPV). In addition, AcMNPV polyhedra production in the IPLB-TN-R cell line occurs later than desirable (beginning at 18 and 39 hours post infection), indicating an inefficient baculovirus replicating cell line. The BTI-TN-5B1-28 embryonic cell line reported by Granados et al. (1986) is moderately susceptible to infection by AcMNPV and *Trichoplusia ni* singly-enveloped nuclear polyhedrosis virus (TnSNPV).

SUMMARY OF THE INVENTION

This invention encompasses two new and useful cell lines from one species of the order Lepidoptera, *Trichoplusia ni* (the cabbage looper). These two new cell lines are BTI-TN-MG1 and BTI-TN-5B1-4. The BTI-TN-MG1 cell line was derived from *Trichoplusia ni* midgut cells and the BTI-TN-5B1-4 was cloned from *Trichoplusia ni* embryonic cell line BTI-TN-5B1-28. Both of these cell lines are highly susceptible to baculoviruses, and said baculoviruses may be useful for the production of pesticides. Both cell lines are also amongst a few which are susceptible to *Trichoplusia ni* singly-enveloped nuclear polyhedrosis virus (TnSNPV). Furthermore, the line derived from *Trichoplusia ni* midgut cells (BTI-TN-MG1) may be particularly useful for studying the mechanism of action of *Bacillus thuringiensis* crystalline insecticidal proteins, which acts on the midgut of the larval stage of several species of lepidoptera.

It is therefore an object of this invention to disclose new cell lines which are useful for the replication of baculoviruses.

It is another object of this invention to disclose the method of establishing these new cell lines.

It is yet another object of this invention to disclose a novel and useful method of establishing insect cell lines.

It is yet another object of this invention to disclose cell lines developed from differentiated tissues of the cabbage looper, *Trichoplusia ni.*

It is yet another object of this invention to disclose a cell line developed from differentiated insect midgut tissue.

It is yet another object of this invention to disclose a method of isolating *Trichoplusia ni* midgut tissue to be used in establishing a *Trichoplusia ni* midgut cell line.

It is yet another object of this invention to disclose a method of replicating baculoviruses using these new cell lines.

It is yet another object of this invention to disclose cell lines which are useful for the study of the mechanism of action of *Bacillus thuringiensis* crystalline insecticidal proteins, or other insecticidal proteins.

It is yet another object of this invention to disclose novel cell lines which may be used for the production of recombinant proteins.

Further objects of the invention will be set forth in the description which follows, and will become apparent to those skilled in the art upon examination of the specification or by practice of the invention.

DETAILED DESCRIPTION OF THE INVENTION

Establishment of New Cell Lines

Two new cell lines were established from Lepidoptera, Noctuidae, *Trichoplusia ni:* BTI-TN-MG1 from midgut tissue and BTI-TN-5B1-4, cloned from the low baculovirus susceptible *Trichoplusia ni* egg cell line BTI-TN-5B1-28. The establishment of the BTI-TN-MG1 cell line requires isolating the midgut tissue of *Trichoplusia ni* and then establishing the cell line from the isolated midgut of *Trichoplusia ni.* The method of isolating the midgut tissue of *Trichoplusia ni* comprised the steps of: a. selecting *Trichoplusia ni* larvae, 15 hours after they molted into the fifth instar (an empirically determined time), b. dissecting midgut tissue from said *Trichoplusia ni* larvae, c. washing the dissected midgut tissue to remove adhering fat body and tracheoblasts and, d. removing the peritrophic membrane (PM) and food bolus.

Following the isolation of the midgut, a cell line was established from the isolated midgut tissue of *Trichoplusia ni,* by a method comprising the steps: a. finely mincing said isolated midgut tissue, with small dissecting scissors, b. shaking (70 cycles/min) said isolated tissue with a gentle proteolytic enzyme (e.g. dispase) (Roberts, *The use of proteolytic enzymes for harvesting insect cell lines which support nuclear polyhedrosis virus replication,* FEMS Microbiology Letters 29: 189–191 (1985)), 1% w/v, 5 units/ml in GTC-100 medium (described in Granados et al., *Replication of the Trichoplusia ni granulosis virus and nuclear polyhedrosis viruses in cell cultures,* Virology, 152:472–476 (1986), which is incorporated herein by reference) for 15 minutes at room temperature, to form dissociated cells and clumps of tissue, c. centrifuging said dissociated cells and said clumps of tissue at 50 g for 5 minutes, d. resuspending said dissociated cells in GTC-100 medium containing 100 μg/ml gentamicin sulfate (Sigma Chemical Co., St. Louis, Mo.) and 250 μg/ml Amphotericin B (Sigma Chemical Co.), e. seeding said cells into wells of a 24 multi-well disposable cell culture plate (Becton Dickinson and Co., Lincoln Park, NJ), f. transferring said dissociated cells to disposable 25 cm$^2$ T flasks, when cells became crowded, g. changing said media every two weeks until the first subculture, approximately two months after the initiation of the cultures, h. maintaining said cell cultures at an appropriate temperature for growth, 28° C. in a modular incubator chamber (Vangard International, Neptune, N.J.), and i. flushing said cultures with atmosphere high in oxygen, such as 95% oxygen/5% carbon dioxide, twice weekly (Riddiford et al., *Culture of the epidermis of the Tobacco Hornworm Manduca Sexta,* TCA Manual 5(1): 975–985 (1979).

Two steps used for establishing the BTI-TN-MG1 cell line were: a. shaking isolated midgut tissue with dispase (70 cycles/minute), and b. periodically flushing midgut cell culture with an atmosphere high in oxygen (95% oxygen). Prior art (Roberts, *The use of proteolytic enzymes for harvesting insect cell lines which support nuclear polyhedrosis virus replication,* FEMS Microbiology Letters 29: 189–191 (1985)) suggests that shaking insect cells in the presence of a gentle proteolytic enzyme (e.g. dispase) may greatly aid in the harvesting of insect cell lines. Other studies concerning the culturing of cell lines mention the importance an atmosphere high in oxygen for establishing and maintaining specific cell lines. Philippe showed that a culture of fat body of *Periplaneta Americana* depends on oxygen (Philippe, *Culture of fat body of Periplaneta Americana: tissue development and establishment of cell lines,* 28: 257–265 (1982)), while Riddiford et al. noted an atmosphere consisting of 95% oxygen, was critical for establishing a cell line of the epidermis of the Tobacco Hornworm *Manduca Sexta* (Riddiford et al., *Culture of the epidermis of the Tobacco Hornworm Manduca Sexta,* TCA Manual 5(1): 975–985 (1979). Both of these teachings were employed in and appear important for establishing the first *Trichoplusia ni* midgut cell line (BTI-TN-MG1).

It is reasonable to suggest, therefore, the same method as utilized in establishing BTI-TN-MG1 may be useful in establishing other insect cell lines. A method for establishing a cell line from isolated tissue of insects could be as follows: a. finely mincing said isolated insect tissue, with small dissecting scissors, b. shaking (e.g. 70 cycles/min) said isolated insect with a gentle proteolytic enzyme (e.g. dispase), 1% w/v, 5 units/ml in GTC-100 medium for 15 minutes at room temperature, to form dissociated cells and clumps of tissue, c. centrifuging said dissociated cells and said clumps of tissue at 50 g for 5 minutes, d. resuspending said dissociated cells in GTC-100 medium containing 100 μg/ml gentamicin sulfate (Sigma Chemical Co., St. Louis, Mo.) and 250 μg/ml Amphotericin B (Sigma Chemical Co.), e. seeding said cells into wells of a 24 multi-well disposable cell culture plate (Becton Dickinson and Co., Lincoln Park, N.J.), f. transferring said dissociated cells to disposable 25 cm$^2$ T flasks, when cells became crowded, g. changing said media every two weeks until the first subculture, approximately two months after the initiation of the cultures, h. maintaining said cell cultures at an appropriate temperature for growth, 28° C. in a modular incubator chamber (Vangard International, Neptune, N.J.), and i. flushing with an atmosphere high in oxygen, such as 95% oxygen/ 5% carbon dioxide, twice weekly.

The BTI-TN-5B1-4 cell line was cloned from a parental cell line (designated BTI-TN-5B1-28). The parental cell line was in the 28th passage and had been established from *Trichoplusia ni* eggs as described by Granados et al. (Virology 152, 472–476, 1986). The clone (BTI-TN-5B1-4) was obtained by diluting the parental cell line and seeding the suspended *Trichoplusia ni* cells into a 96 well microplate (0.1 ml cell suspension/well). The BTI-TN-5B1-4 clone arose from a single cell and, one week later, the cells were transferred into a 24 well microplate as the cell numbers increased. Within one month, the cells (BTI-TN-5B1-4) were transferred to a 25 cm$^2$ T flask for routine subculturing.

Thus, the method for establishing cell line BTI-TN-B1-4 can be summarized as follows: a. diluting parental *Trichopulsia ni* cell line (BTI-TN-5B1-28), b. seeding the suspended *Trichopulsia ni*. cells into a 96 well microplate (0.1 ml cell suspension/well), c. transferring the cells, arising from a single BTI-TN-5B1-28 cell, from a well of said 96 well microplate to a 24 well microplate as the cell numbers increase, d. transferring BTI-TN-5B1-4 cells to a 25 cm$^2$ flask for routine subculturing.

BTI-TN-MG1 and BTI-TN-5B1-4 cells were maintained in TNM-FH medium (TNM-FH is prepared as follows: to prepare 100 ml, a. combine 900 ml of Graces medium, 80 ml of Fetal Bovine Serum, 3.0 grams of Lactalbumin hydrolysate, and 3.0 grams Yeastolate, b. stir vigorously on magnetic stirrer to dissolve powdered ingredients, c. measure pH, pH of a solution should be between 6.40–6.45 (adjust if necessary with: a. 1.0N KOH (increases pH) or b. 1.0N HCl (decreases pH)), d. measure osmotic pressure (Optimum osmolality is between 360–380 milliosmols (MOSM)), adjust if necessary with: a. glucose increases osmotic pressure (OP) (1 g anhydrous D-glucose/0.51→change in OP of 7) or b. H$_2$O decreases OP (7 ml H$_2$O+100 ml→change in OP of −10 MOSM)) in Corning, T-25 cm$^2$ tissue culture flasks and were subcultured under aseptic conditions when a confluent monolayer is observed. Cell lines BTI-TN-MG1 and BTI-TN-5B1-4 were switched from GTC-100 medium to the richer TNM-FH medium at passages 167 and 258 respectively. Cells were detached from flask walls by either a solid "wrist snap" of the flask or by using a rubber policeman. Initial seeding densities are between 2–3×10$^5$ cells/ml which is represented by split ratios of 0.8–1 ml cell suspension to 4.2–4 ml fresh TNMFH, respectively for MG1 cells, and 0.3–0.5 ml cell suspension to 4.7–4.5 ml medium for 5B1-4 cells.

Both newly established cell lines were adapted from GTC-100 medium to TNM-FH at least 4 months prior to the initiation of the virus susceptibility experiments. When the susceptibility experiments began, the BTI-TN-MG1 and BTI-TN-5B1-4 cell line had reached their 223rd and 287th passages respectfully. The cell lines were subcultured twice weekly at 1/5 seeding ratios. The BTI-TN-MG1 was detached from the flask by means of a cell scraper and the BTI-TN-5B1-4 was detached by a "wrist snap". Both lines were frozen in liquid nitrogen for safekeeping; BTI-TN-MG1 at passage 220 and BTI-TN-5B1-4 at stage passage 331.

Deposited Material

Both cell lines have been accepted for deposit by the American Type Culture Collection, 12301 Parklawn Drive, Rockville, Md. 20852, and will be made available under the terms and conditions imposed by the Budapest Treaty. The accession numbers of the cell lines are as follows: BTI-TN-MG1, ATCC, CRL 10860, and BTI-TN-5B1-4, ATCC CRL 10859.

Cell Growth Curves

Cells in log phase were subcultured into 25 cm$^2$ T flasks (Corning Glass Works, Corning, N.Y.). Cell densities were determined by counting the cell numbers within a microscope reticle of which the area at a certain objective was known. The cell densities in five areas of each flask were determined at 24 hr. intervals. Cell population doubling time was calculated using the exponential formula described by Hayflick (*Subculturing human diploid fibroblast cultures*, Kruse and Patterson, eds., New York: Academic Press 1973, pp. 220–223).

Test of Susceptibilities to Nuclear Polyhedrosis Viruses

Cells were cultured in 25 cm$^2$ T flasks and when the cell cultures were in the log growth phase, cell densities were determined by using a microscope reticle. The medium was aspirated and 1 ml of virus inocula was added to each flask (the inocula were prepared by diluting infectious media with TNM-FH medium so that all individual flasks were infected at a multiplicity of infection (MOI) of 5). The *Autographa californica* multiply-enveloped nuclear polyhedrosis virus (AcMNPV) infectious medium used was 2nd passage produced in the IPLB-SF-21AE cell line. The *Trichoplusia ni* singly-enveloped nuclear polyhedrosis virus (TnSNPV) was a plaque purified isolate from which 1st passage infectious medium was produced in BTI-TN-5B1-4 cells. Polyhedra containing cells were counted at 4 days post inoculation (p.i.).

Isozyme Analysis

Cell samples were prepared and run on gels according to Corsaro and Fraser (*Characterization of clonal populations of the Heliothis zea cell line IPLB-HZ 1075*, In Vitro Cell. Dev. Bio. 23(12):855–862 (1987)). Briefly, monolayers of cells were harvested from 25 cm$^2$ T flasks. The cells were pelleted at 1800 g for 10 min, resuspended in 500 μl of cell grinding solution (0.15M Tris-Cl, pH 7.1, 46 mM citric acid, 10% sucrose, 1% Triton X-100, and 0.02 mM bromphenol blue), and lysed by crushing cells in a 0.5 ml micro tissue homogenizer. The lysate was cleared by centrifugation at 15,000 g for 3 minutes and the process was repeated to crush the cells for a second time. The cleared supernatants were stored in 30 μl aliquots at −70° C.

For sample separation, 0.75 mm vertical gels were used, 4.75%/0.25% acrylamide/bisacrylamide in 39 mM Tris HCl, pH 7.1, 8.5 mM sodium citrate (2×TC buffer). 10–20 μl of lysate were loaded onto each well, and the samples were separated at 350 V for 2 hours in TC buffer. The gels were stained for enzymes lactate dehydrogenase (LDH) and malate dehydrogenase (MDH) following the protocol of Harris and Hopkinson (*Handbook of Enzyme Electrophoresis in Human Genetics*, Amsterdam: North Holland Publishing Co. (1977), incorporated herein by reference, pages 68, 69).

Cell Line Growth Characteristics

Although oxygen supplementation was needed to promote the initial establishment of the primary midgut cell line, once they were established on a regular subculturing schedule, non-oxygen supplemented sister flasks were derived from them. After a year of evaluation, it was concluded that the non-supplemented cells grew equally as well, and supplementation was discontinued.

The BTI-TN-MG1 cells often appear as a mixture of round and spindle shapes and are considered medium size. The cytoplasm is lightly granulated, with a well defined nucleus containing one or two (usually) nucleoli. These cells attach firmly to tissue culture treated flasks and form confluent monolayers. When these cells reach the stationary phase however, they tend to clump up and float. A confluent monolayer can be expected after three to four days at 28° C.

In preliminary electron microscopy studies the BTI-TN-MG1 cells did not exhibit the ultrastructural features of cells obtained from larvae. For example, microvilli could not be detected in the midgut cells.

The BTI-TN-5B1-4 insect cell line was derived from eggs of the cabbage looper, *Trichoplusia ni*. These cells (diameter approximately 20 μm) are generally larger then BTI-TN-MG1 and also appear as a mixture of round and spindle shapes. The cytoplasm is also lightly granulated and the nucleus usually contain three to four nucleoli. As with BTI-TN-MG1 cells, BTI-TN-5B1-4 cells attach firmly to flasks and form confluent layers after three to four days at 28° C.

The cell population doubling times for BTI-TN-MG1, and BTI-TN-5B1-4 are 25 and 26 hours respectively. These doubling times are similar to those reported for other established lepidopteran cell lines, although the new *Trichoplusia ni* lines detailed in this patent application have a slower doubling time than prior cell lines ((Hink et al., *Metabolism and characterization of insect cell cultures*, in vol. 10 "Comprehensive Insect Physiology, Biochemistry, and Pharmacology" (Kerkut and Gilbert, eds., Pergamon Press, Oxford, U.K.), pp. 547–570 (1985)).

Susceptibilities to Viruses

The cell lines BTI-TN-MG1 and BTI-TN-5B1-4 were inoculated with baculoviruses AcMNPV and TnSNPV (both of which are members of the family Baculoviridae) at an MOI of 5 and then incubated. Polyhedra were present 14 to 16 hours post baculovirus infection in both cell lines. The percentages of polyhedra-containing (typical cytopathic effect of NPV infection) at 4 days p.i. are shown in Table 1. The number of polyhedra was determined by sonicating the infected cells, then centrifuging said cells, and finally counting the amount of polyhedra using a hemocytometer. The number of cells in each cell line was previously determined. Both cell lines were highly susceptible to AcMNPV infection with 91.5% of BTI-TN-MG1 cells and >95.0 of BTI-TN-5B1-4 cells containing polyhedra. The midgut cell line had lower susceptibility to TnSNPV with 76% polyhedra-containing cells, while the BTI-TN-5B1-4 cell line had high susceptibility with 99% polyhedra-containing cells.

Isozyme Analysis

Isozyme analysis was used to determine the characteristic of the two new cell lines (to confirm that BTI-TN-MG1 and BTI-TN-5B1-4 are of the same origin as the TN-368 cell line). The MDH and LDH isozyme band relative mobility values (RF) of the two cell lines were compared with each other and with those of Lepidopteran cell lines from *Heliothis zea* IPLB-HZ1075/UND-K, *Spdoptera frugiperda* IPLB-SF21AE, *Trichoplusia ni* TN368, and *Mamestra brassicae* IZD-MB-0507. The Rf are presented in Table 2, and were calculated using the banding pattern of IPLB-HZ1075/UND-K as reference (Rf=1.0).

The banding patterns and their corresponding Rf confirm that BTI-TN-MG1 and BTI-TN-5B1-4 were of the same origin as the TN-368 cell line and distinct from the other cell lines tested. The IPLB-HZ1075/UND-K and IPLB-SF21AE bands co-migrated in MDH, but were different in LDH (as in Corsaro and Fraser). The Rf of IZD-MB-0507 in LDH and MDH were very similar to those of the *Trichoplusia ni* cell lines.

The two newly established cell lines described herein possess characteristics that make them potentially valuable cell lines in research and commercial applications. Both of these new cell lines may be used for replicating baculoviruses, which may be used as insecticides or for the production of recombinant vaccines, antibodies, antitoxins, and the like.

This is the first established midgut cell line from any species of insect. Since the midgut of insects is the primary site of entry and action by insect pathogens (e.g. *Bacillus thuringiensis* insecticidal crystal proteins), the BTI-TN-MG1 line may be especially useful in membrane receptor studies of specific insecticidal proteins, and in toxicity studies of said insecticidal proteins (Hofmann et al., *Specificity of Bacillus thuringiensis δ-endotoxins is correlated with the presence of high-affinity binding sites in the brush border membrane of target insect midguts*, Proc. Natl. Acad. Sc. 85:7844–7848 (1988)).

Both the BTI-TN-MG1 and the BTI-TN-5B1-4 cell lines possess excellent growth characteristics, and are susceptible to AcMNPV and TnSNPV. Furthermore, BTI-TN-5B1-4 cloned from parental egg *Trichoplusia ni* cell line BTI-TN-5B1-28 displays improved susceptibility, over its parental line, to TnSNPV and AcMNPV, and is a particularly efficient cell line supporting the replication of baculoviruses.

TABLE 1

Susceptibilities of the Two Cell Lines to Two Nuclear Polyhedrosis Viruses*

| Cell line | Virus | Number of Cells counted | Percentage of Polyhedra-containing Cells** |
|---|---|---|---|
| BTI-TN-5B1-4 | AcMNPV | ND*** | >95.0 |
| BTI-TN-MG1 | AcMNPV | 648 | 91.5 |

TABLE 1-continued

Susceptibilities of the Two Cell Lines to Two Nuclear Polyhedrosis Viruses*

| Cell line | Virus | Number of Cells counted | Percentage of Polyhedra-containing Cells** |
|---|---|---|---|
| BTI-TN-MG1 | TnSNPV | 544 | 76.1 |
| BTI-TN-5B1-4 | TnSNPV | ND*** | 99.0 |

*Cells were cultured in TNM-FH medium and infected at an MOI of 5.
**Counting was conducted at 4 days p.i.
***ND = not determined

TABLE 2

Relative Mobility (Rf Values of Isozymes LDH and MDH)

| Cell Line Designation | LDH | MDH | Insect of Origin |
|---|---|---|---|
| BTI-TN-MG1 | 0.486 | 2.0 | Trichoplusia ni |
| BTI-TN-5B1-4 | 0.486 | 2.0 | Trichoplusia ni |
| TN-368 | 0.486 | 2.0 | Trichoplusia ni |
| IPLB-SF21AE | 0.729 | 1.0 | Spodoptera frugiperda |
| IPLB-HZ1075/UND-K | 1.0 | 1.0 | Heliothis zea |
| IZD-MB-0507 | 0.499 | 2.09 | Mamestra brassicae |

BTI-TN-5B1-4 in Serum-Free Medium

BTI-TN-5B1-4 cells in TNMFH serum containing medium were adapted to SF900 serum-free medium (Gibco, BRL, Grand Island, N.Y. 14072) at passage number 289. These cells in SF900 were subsequently adapted to EX-CELL 400 serum free medium (JRH BioSciences, 13804 W. 107th St. Lenexa, Kans. 66215) at passage number 37. The adaptations to both serum-free media were done sequentially, as commonly practiced in the art and as outlined by GIBCO Laboratories (GIBCO Laboratories, "SF-900 serum-free Insect Cell Culture Medium with L-glutamine, Catalog Number 350-0900", November 1989, 4 pgs.). By the 75th passage of the cells in EX-CELL 400 the doubling time for the cells was approximately 21 hours. These cells are large and appear as a mixture of round and spindle shapes. The cytoplasm is lightly granulated and the nucleus usually contains three to four nucleoli. BTI-TN-5B1-4 cells attach moderately to flasks, form confluent monolayers after three to four days after passage, and reach a maximum cell density of $2.75 \times 10^6$ cell/ml (in 25 cm$^2$ T flask). Cells were incubated at 28° C. and at ambient oxygen level.

Baculovirus Plaque Assay in BTI-TN-5B1-4 Cells in Serum-Free Medium

BTI-TN-5B1-4 cell susceptibility to viral infection while in serum-free medium (EX-CELL 400) was in part determined by a plaque assay. The protocol for the plaque assay is as follows: a. using 6-well plate, dilute the cells to $1 \times 10^6$ cells/ml (BTI-TN-5B1-4 cells were at passage 58 in EX-CELL 400 medium when assayed). Sf 9 cells (Summers and Smith, 1987) and Sf 21 cells (Vaughn, 1977) are typically used as standards for titering viruses and were used in this plaque assay (Sf 9 and Sf 21 cells in EX-CELL CELL 400 were at passages 16 when assayed), b. add BTI-TN-5B1-4 cells to the wells and allow them to attach for 15-20 minutes. Check with microscope for cell damage and dispersion. While the cells are attaching, prepare serial 10-fold dilutions of AcMNPV as follows: (all viral dilutions are done in Grace's Basal Medium (GBM) (no FBS).) Remove 20 μl of AcMNPV inoculum and add to 2.2 ml GBM. This will give a $10^{-2}$ dilution. 2) transfer 0.2 ml of the $10^{-2}$ dilution to 2 ml GBM for a $10^{-3}$ dilution. Continue to transfer 0.2 ml from one dilution to the next making sure the final volume in each dilution is 2 ml; continue diluting until $10^{-8}$ viral dilution., c. add mixed virus dilutions to wells (be sure to have replica wells for each dilution) and gently rock plates to distribute the virus. Seal plates with black electrical tape., d. using the Sorvall GLC-2B centrifuge and the weight matched centrifuge carriers, centrifuge the plates at $1000 \times g$ (2400 RPM) for 1 hr. While the cells and virus are spinning, prepare the agarose overlay as follows: 1) remove the large glass test tubes containing the agarose (0.42 g/14 ml GBM=3%) from 4° C. and take off the black tape seal. With the metal cap still on, microwave on high for about 30 seconds. Mix the agarose carefully and place in a 39° C. water bath for 20-30 minutes., 2) place enough complete medium containing gentamicin (200 μg/ml) and/or X-Gal (150 μg/ml) in the 39° C. water bath and allow it to reach 39° C. (takes 20 to 30 minutes)., e. after removing the plates from the centrifuge and examining wells for good cell dispersion, the medium is aspirated from each well using a 1 ml blue pipet tip (a "cleaner" section will be evident in each well, this is where aspiration should be performed)., f. quickly add 14 ml of warmed medium (with supplements) to test tube containing the agarose (final concentration of 1.5%)., g. carefully add 2 ml agarose overlay to each well being sure not to introduce bubbles, h. allow plates to sit for 15-20 minutes undisturbed, before taping and placing in humidified bags., i. incubate plaque assays for 5-7 days at 28° C., j. count plaques using the Zeiss inverted microscope from replica wells for each dilution and record.

The results of the plaque assay are presented below in Table 3.

TABLE 3

Extracellular Virus Titers for Cell Lines in EX-CELL 400 Medium

| Cell Line | PFU/ml |
|---|---|
| Sf 21 | $1.4 \times 10^7$ |
| Sf 9 | $6.3 \times 10^7$ |
| BTI-TN-5B1-4 | $2.0 \times 10^7$ |

*PFU = Plaque forming units

Occlusion Bodies Assay for BTI-TN-5B1-4 in Serum-Free Medium

BTI-TN-5B1-4 susceptibility to viral infection while in serum-free medium (EX-CELL 400) was also measured by occlusion body assay (BTI-TN-5B1-4 cells were at passage number 58 in EX-CELL 400 medium when assayed). The occlusion body assay was performed as follows: a. replicate wells of a 24 well plate were seeded with BTI-TN-5B1-4 cell in EX-CELL 400 at cell densities of $5 \times 10^5$ cells/ml, b. the cells are then infected with wild type AcMNPV non-occluded virus at MOI=10 and incubated for 96 hours, c. following incubation, all cells plus the medium were removed from each well by pipeting vigorously, d. cells are pelleted at high speed in a microcentrifuge for 5 minutes, e. the pellet was resuspended in 500 μl deionized water by sonicating for 5-10 seconds, f. steps d and e were repeated, g. step d was repeated and then the pellet was resuspended in 1 ml deionized water by sonicating for 5-10 seconds, and h. occlusion bodies were counted twice in 20 μl samples using a hemocytometer. Sf 9 cells (Summers and Smith, 1987) and Sf 21 cells (Vaughn, 1977) are typically used as standard occlusion bodies and were also assayed using the above procedure (Sf 9 and Sf 21 cells in EX-CELL 400 were at passages 16 when assayed).

The results of the occlusion bodies assay are presented below in Table 4.

TABLE 4

| Occlusion Bodies for Cell Lines in EX-CELL 400 | |
|---|---|
| Cell Line | No. OBs/$10^6$ cells |
| Sf 21 | $2.1 \times 10^7$ |
| Sf 9 | $1.3 \times 10^7$ |
| BTI-TN-5B1-4 | $6.5 \times 10^7$ |

The results of the susceptibility tests (plaque assay and occlusion bodies assay) performed on BTI-TN-5-B1-4 cells in serum-free medium indicate the cells are susceptible to viral infection while in serum-free medium. The number of plaque forming units/ml produced by BTI-TN-5-B1-4 infected cells is comparable to Sf 9 cells (Table 3) and number of occlusion bodies per million cells is approximately 3 fold and 6 fold greater than Sf 21 and Sf 9 cells respectively (Table 4). Therefore, BTI-TN-5-B1-4 are susceptible to baculoviruses in serum-free medium as well as serum-containing medium.

The foregoing description has been directed to particular embodiments of the invention in accordance with the requirements of the Patent Statutes for the purposes of illustration and explanation. It will be apparent, however, to those skilled in this art that many modifications, variations and changes will be possible without departure from the scope and spirit of the invention. It is intended that the following claims be interpreted to embrace all such modifications.

What is claimed is:

1. An isolated homogeneous cell line from the eggs of *Trichoplusia ni*, having all the identifying characteristics of BTI-TN-5-B1-4, ATCC CRL 10859.

2. The cell line of claim 1, wherein said cell line is adapted to serum-free medium by serial adaptation.

3. The cell line of claim 2, wherein said cell line is infected by a baculovirus and supports the replication of said baculovirus.

4. The cell line of claim 1, wherein said cell line is infected by a baculovirus and supports the replication of said baculovirus.

* * * * *